(12) United States Patent
Huthmacher

(10) Patent No.: US 11,486,872 B2
(45) Date of Patent: *Nov. 1, 2022

(54) METHOD AND DEVICE FOR MONITORING A TEXTURING PROCESS

(71) Applicant: Oerlikon Textile GmbH & Co. KG, Remscheid (DE)

(72) Inventor: Jörg Huthmacher, Marl (DE)

(73) Assignee: Oerlikon Textile GmbH & Co. KG, Remscheid (DE)

(*) Notice: Subject to any disclaimer, the term of this patent is extended or adjusted under 35 U.S.C. 154(b) by 142 days.

This patent is subject to a terminal disclaimer.

(21) Appl. No.: 16/960,400

(22) PCT Filed: Jan. 2, 2019

(86) PCT No.: PCT/EP2019/050015
§ 371 (c)(1),
(2) Date: Jul. 7, 2020

(87) PCT Pub. No.: WO2019/137835
PCT Pub. Date: Jul. 18, 2019

(65) Prior Publication Data
US 2020/0340972 A1    Oct. 29, 2020

(30) Foreign Application Priority Data
Jan. 9, 2018 (DE) .................. 10 2018 000 124.6

(51) Int. Cl.
*G01N 33/36* (2006.01)
*B65H 59/40* (2006.01)
(Continued)

(52) U.S. Cl.
CPC .......... *G01N 33/365* (2013.01); *B65H 59/40* (2013.01); *B65H 63/062* (2013.01); *D01H 13/32* (2013.01); *B65H 2557/65* (2013.01)

(58) Field of Classification Search
CPC ................... G05B 23/0229; G05B 23/0232
See application file for complete search history.

(56) References Cited

U.S. PATENT DOCUMENTS 4,754,410 A * 6/1988 Leech ................ D01H 9/00
706/45
5,497,335 A * 3/1996 Hoeller ............... D01H 13/32
139/1 R
(Continued)

FOREIGN PATENT DOCUMENTS

DE        19614027        1/1998
DE        10237978        3/2004
(Continued)

*Primary Examiner* — Shaun R Hurley
*Assistant Examiner* — Patrick J. Lynch
(74) *Attorney, Agent, or Firm* — BainwoodHuang

(57) ABSTRACT

A method for monitoring a texturing process for producing crimped threads is presented, in which a thread tension is measured continuously on the textured thread and in which the thread tension measuring signals are captured and analyzed continuously, at least in one time interval, characterized in that a sequence of the thread tension measuring signals occurring in the time interval is analyzed with a machine learning program for the early diagnosis of one of a plurality of fault sources.

16 Claims, 7 Drawing Sheets

Figure 1:
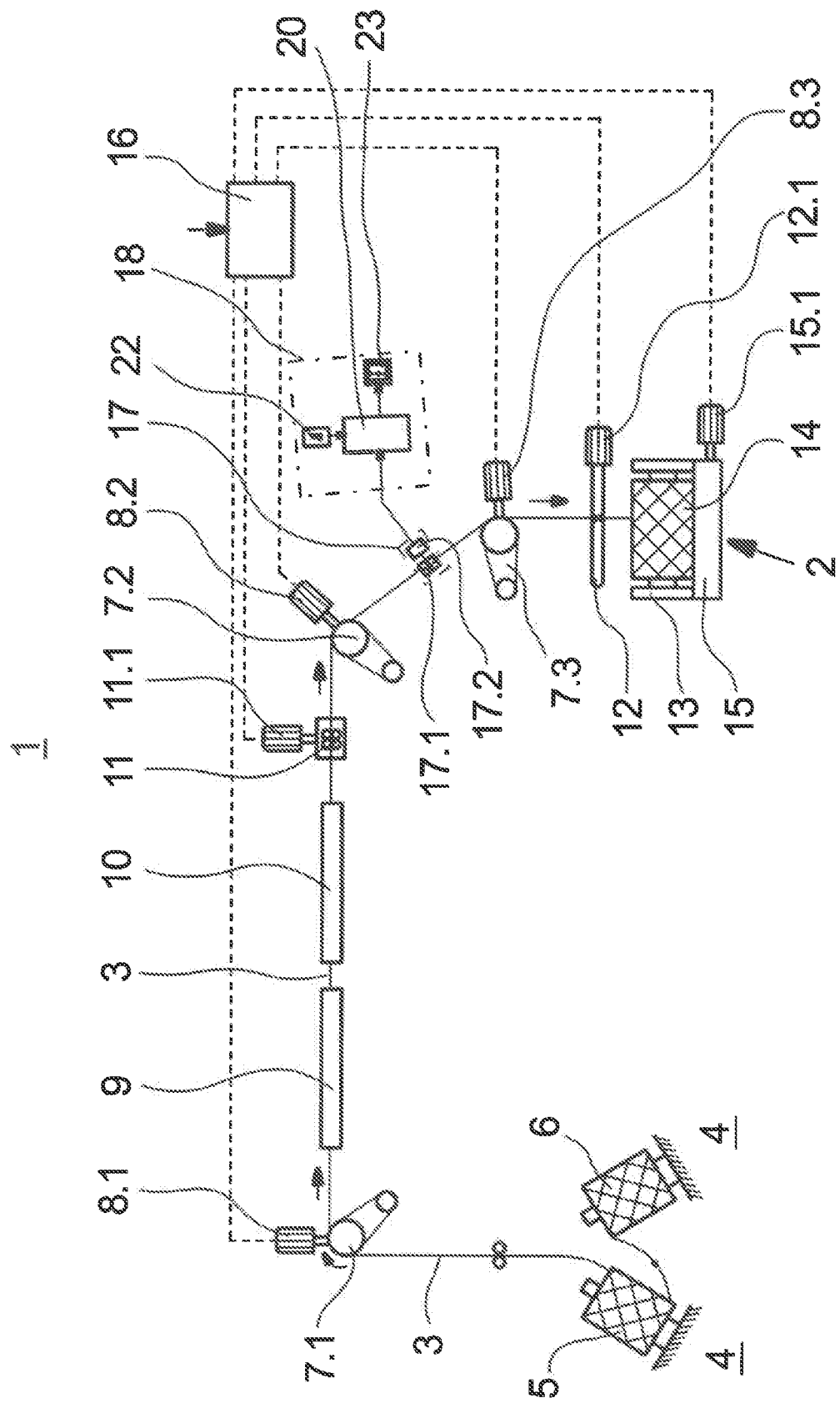

(51) Int. Cl.
    *B65H 63/06* (2006.01)
    *D01H 13/32* (2006.01)

(56) References Cited

U.S. PATENT DOCUMENTS

| | | | |
|---|---|---|---|
| 5,682,146 A | 10/1997 | Neumann | |
| 6,304,795 B1* | 10/2001 | Reist | B07C 1/02 |
| | | | 700/219 |
| 2003/0141404 A1* | 7/2003 | Lannes | B65H 18/00 |
| | | | 242/541.7 |
| 2020/0027339 A1* | 1/2020 | Gutberlet | D01H 13/32 |
| 2021/0122604 A1* | 4/2021 | Huthmacher | G01L 5/102 |
| 2021/0188590 A1* | 6/2021 | Huthmacher | G01L 5/10 |

FOREIGN PATENT DOCUMENTS

| | | |
|---|---|---|
| WO | 20150052624 | 4/2015 |
| WO | 20180224398 | 12/2018 |

* cited by examiner

METHOD AND DEVICE FOR MONITORING A TEXTURING PROCESS

The invention relates to a method for monitoring a texturing process for producing crimped threads as disclosed herein, and a device for monitoring the texturing process as disclosed herein.

A generic method and a generic device for monitoring a texturing process for producing crimped threads are known, for example, from DE 196 14 027 A1.

In the texturing of synthetic threads, it is customary to monitor the production process continuously in order to thus obtain a possible stable process management and, in particular, as far as possible, a stable product quality in the crimped thread. The monitoring of a thread tension on the running thread has proven successful here in detecting process faults and/or product fluctuations. In the known method and the known device for monitoring the texturing process, the thread tension on the thread is continuously measured for this purpose. The generated thread tension measuring signals are compared with a threshold value of a permissible thread tension. The signal characteristic of the thread tension measuring signals measured continuously in a time interval indicates possible tolerance deviations here. Different signal characteristics of the measuring signals can be detected here depending on the respective fault in the process. Experienced operators can thus use a measuring signal characteristic of the thread tension to identify possible sources of faults in the texturing process.

However, the known method and the known device for monitoring the texturing process have the considerable disadvantage that only the measuring signal characteristics which exceed a threshold value of the thread tension are used for the analysis. Impermissible product limits resulting in a defective quality of the thread are therefore already reached. In addition, the known method and the known device have the further disadvantage that an identification of possible fault sources depends entirely on the experience of the respective operator.

The object of the invention is therefore to develop the generic method and the generic device for monitoring a texturing process for producing crimped threads in such a way that an improved process management becomes possible for the production of consistent thread qualities.

A further aim of the invention is to provide a generic method and a generic device for in monitoring a texturing process with which it is possible to identify process faults as early as possible and eliminate them quickly and in a targeted manner.

This object is achieved according to the invention by a method with the features as disclosed herein and by a device with the features as disclosed herein.

Advantageous developments of the invention are defined by the features and feature combinations as disclosed herein.

The invention is based on the realization that the sequence of measuring signals occurring in a time interval has specific characteristics which manifest themselves in the signal characteristics and can be used in each case as a process control index. The sequence of thread tension measuring signals occurring in the time interval is thus analyzed according to the invention with a machine learning program for the early diagnosis of one or more fault sources. Specific measured value changes in the thread tension occurring in a time sequence can thus be identified even at an early stage on the basis of a known fault source. The changes in the measuring signals typical of a fault source can thus be identified even at an early stage without the thread tension measured value previously exceeding a threshold value. The interdependence of the measuring signals based on a fault source occurs independently from a threshold value of the thread tension. Typical features for identifying the fault source can thus be derived from an analysis of the measuring signal changes. The machine learning program enables a fast and complex analysis of a multiplicity of measuring signals so that their interdependencies are quickly analyzed, particularly in time intervals, and a fault source is thus reliably and quickly identifiable.

Since the change in the measuring signals due to a fault source causes individual characteristic temporal changes depending on the fault source, one method variant is particularly advantageous for obtaining identifications of the fault source which are as conclusive as possible. The sequence of the thread tension measuring signals is thus preferably recorded and analyzed as an analysis graph.

In order to be able to handle, in particular, the permissible changes in the thread tension differently from an impermissible change in the thread tension which exceeds a predefined threshold value, the method variant is particularly advantageous in which a temporal sequence of thread tension measuring signals is recorded and analyzed as a fault graph if a threshold value of the thread tension is exceeded. The threshold value can comprise, for example, an upper limit value and a lower limit value of the thread tension, and also a tolerance range.

Due to a multiplicity of measuring signals which are continuously awaiting analysis, the method variant in which the analysis of the thread tension measuring signals is performed by at least one machine learning algorithm of the machine learning program has proven particularly successful. An artificial intelligence can thus be used to perform structured analyses and enable the identification of the fault source in the shortest analysis times even with a large data volume. For this purpose, however, it is necessary for the machine learning algorithm to refer initially to determined basic data for the learning. To do this, for example, analyzed analysis graphs and analyzed error graphs are transferred to the machine learning algorithm at the beginning of a process for learning purposes. After a learning phase, it is possible for the machine learning algorithm to perform a unique identification of the respective fault source independently through analysis of the measuring signals or analysis graphs or error graphs.

In order to simplify the identification in the case of a multiplicity of fault sources, it is further provided that a plurality of fault graphs are assigned to the analysis graphs and/or the error graphs, wherein each of the fault sources is determined by one of the fault graphs. Fault graphs of this type are used to train the machine learning program so that early identification of the fault source of possible during the analysis of analysis graphs or error graphs.

According to one particularly advantageous method variant, the machine learning program attains an operational status of completed training after one learning phase. The input of fault graphs is no longer required and the machine learning program is capable of analyzing the measured error graphs and assigning them where appropriate to a known fault source.

If unknown fault sources occur which are not identifiable, the machine learning algorithm can be exchanged for external training in order to be able to continue the production with a retrained machine learning algorithm. The diagnostic system can thus be constantly extended with new, hitherto unknown, fault sources.

Operating errors or incorrect settings of a process unit or material faults or wear of a thread-guiding element or a thread knot or other product defects are identifiable here as fault sources. The early diagnosis of possible fault sources even before a thread tension threshold value is reached is thus particularly suitable for carrying out, for example, preventive maintenance on process units. Signs of wear, for example, of the thread-guiding elements can thus be counteracted early.

However, for the automation of the respective texturing process, it is also possible for a control command for a process change to be triggered following identification of the fault source or following assignment to one of the fault graphs. The process change could, for example, be an early bobbin exchange in order to prevent a thread knot from becoming entrained. Alternatively, however, it is also possible to send a specific operating instruction to the operator via a signaling.

The device according to the invention for monitoring the texturing process for producing crimped threads achieves the object by forming the data analysis device by means of a diagnostic unit by which the thread tension measuring signals are analyzable with a machine learning program for identifying one of a plurality of fault sources. The thread tension measuring signals occurring in the time interval can thus be used directly in the texturing process for diagnosing a fault source.

The diagnostic unit has at least one programmable learning processor to run the machine learning program. The learning processor can be coupled directly to the thread tension measuring device.

To optimize the machine learning program and to improve diagnostic reliability, it is further proposed that the learning processor is optionally coupled for training purposes to an input unit by means of which one or more fault graphs are loadable. Typical fault graphs, in particular, are fed to the machine learning program for learning. Following a learning phase and on completion of training, the learning processor is ready for use without a connection to the input unit.

So that an operator is informed of the respective process sequence in the process management, the advantageous development of the device according to the invention is used in which the learning processor is coupled to an output unit by means of which an identification of one of the fault sources or an assignment of the analyzed error graphs to a fault graph is visualizable. This output unit can advantageously be coupled wirelessly to the learning processor and can represent any type of device on which a display is possible.

In order to obtain a system which is as autonomous as possible for the diagnosis, it is further provided that the learning processor has a neural network to run the machine learning program. The large data volumes of thread tension measuring signals can thus be analyzed by an artificial intelligence.

In order to monitor a plurality of processing stations in a texturing machine, the device according to the invention is advantageously usable in the development in which the learning processor is disposed physically separated from the input unit and the output unit. It is possible here for the learning processor to be in contact with a plurality of input units and, in particular, with a plurality of output units. The connection can be configured wirelessly so that the learning processor could be configured, for example, in a virtual space also.

The device variant according to the invention in which the diagnostic unit is connected to a machine control unit by means of which a control command for the process change is executable is advantageously used for automation. Thus, for example, following identification of a thread knot, a measure could be instigated in order to entrain the thread knot at the start or at the end of a wound bobbin.

The method according to the invention for monitoring a texturing process is described in detail below on the basis of some example embodiments of the device according to the invention with reference to the attached figures.

Figure 2:
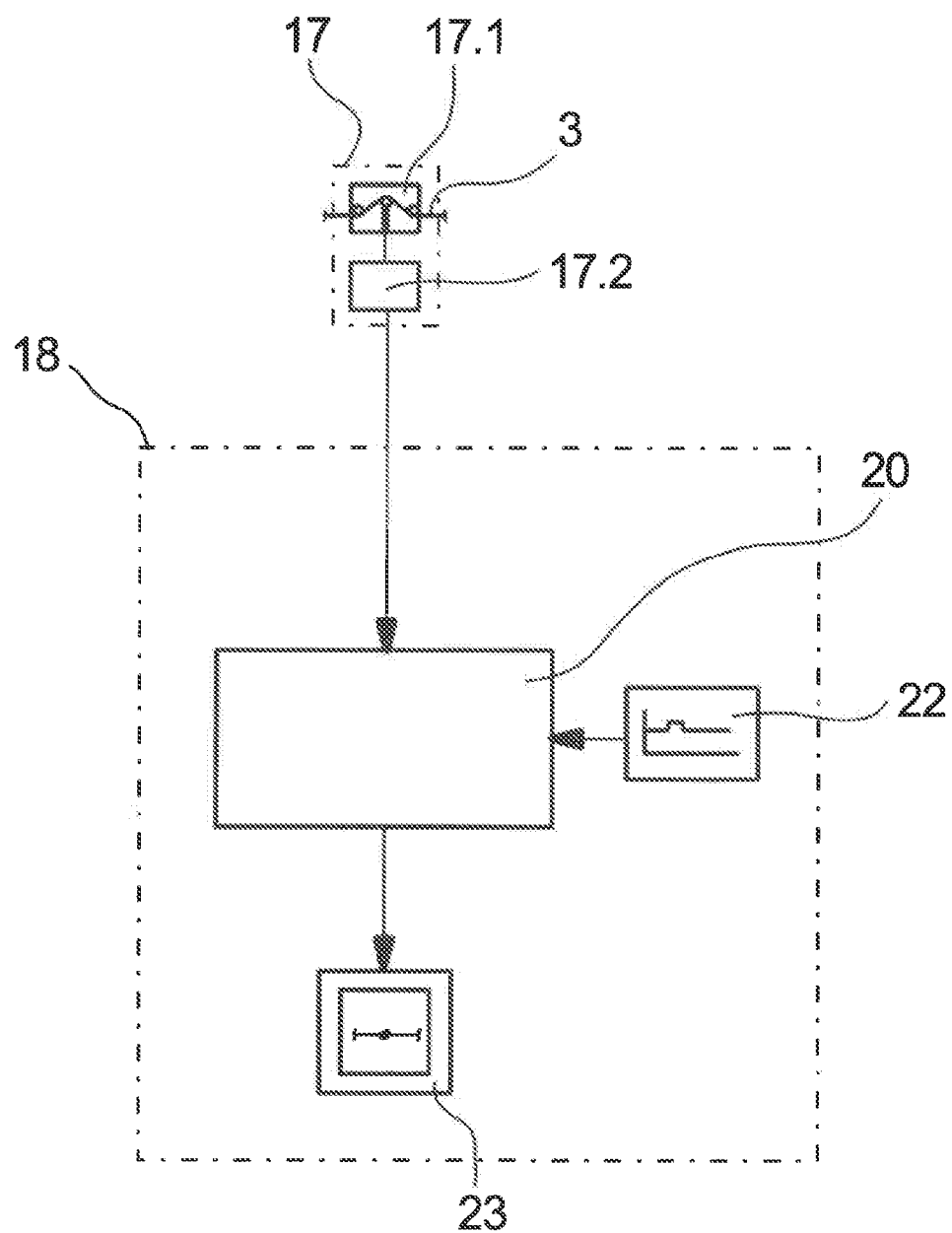
Figure 3:
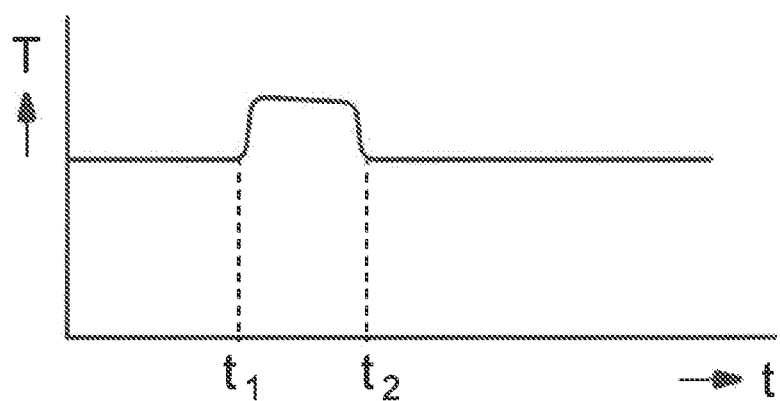
Figure 4:
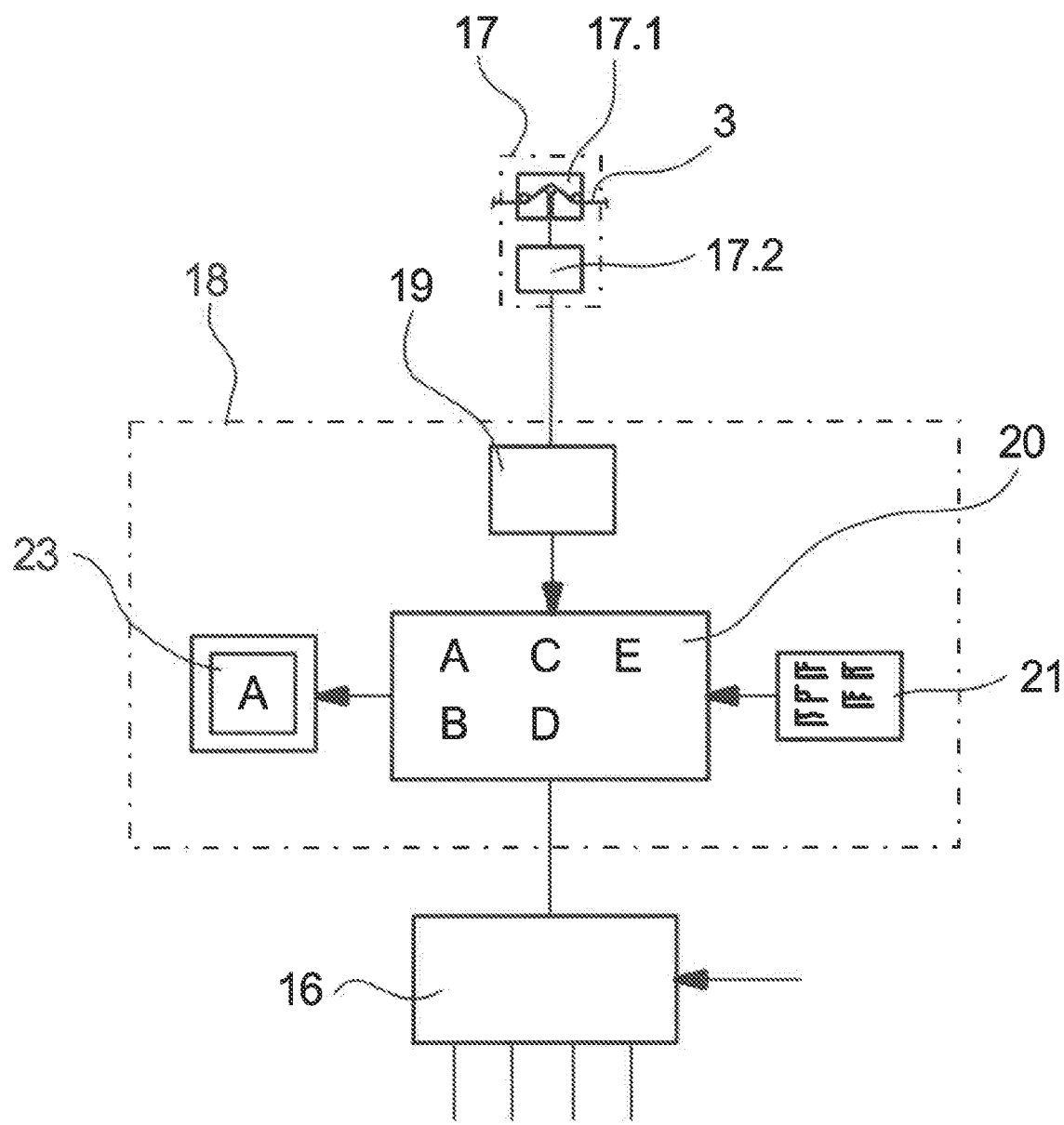
Figure 5:
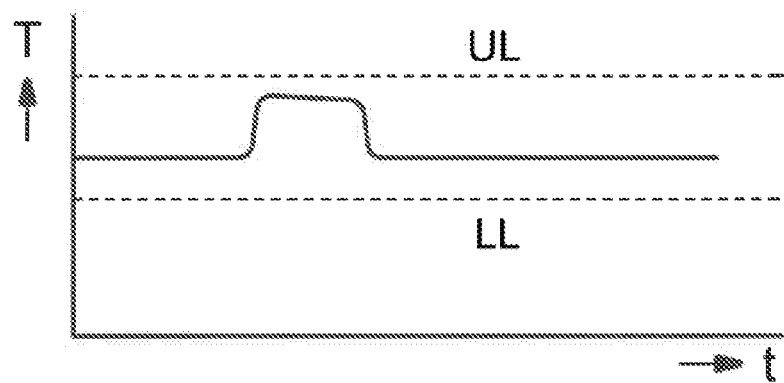
Figure 6:
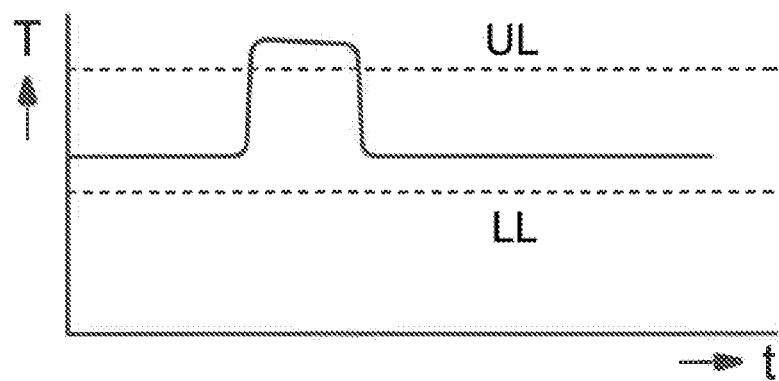

In the figures:

FIG. 1 shows schematically an example embodiment of a texturing process for producing a crimped thread, FIG. 2 shows schematically an example embodiment of the device according to the invention for monitoring the texturing process according to FIG. 1, FIG. 3 shows schematically a thread tension diagram with a sequence of measuring signals, FIG. 4 shows schematically a further example embodiment of the device according to the invention for monitoring the texturing process according to FIG. 1, FIG. 5 shows schematically an analysis graph with a time sequence of a plurality of thread tension measuring signals, FIG. 6 shows schematically an error graph with a time sequence of a plurality of thread tension measuring signals, FIG. 7 to FIG. 11 show schematically a plurality of fault graphs in each case with a measuring signal characteristic of the thread tension of different fault sources.

FIG. 1 shows schematically an example embodiment of a texturing process for producing a crimped thread. The texturing process is described here by way of a processing station of a texturing machine. Texturing machines of this type normally have a multiplicity of processing stations in order to texture a multiplicity of synthetic threads in parallel alongside one another. FIG. 1 shows schematically a processing station 1 and a bobbin station 2 of a texturing machine of this type. The processing station 1 has a creel 4 in which a supply bobbin 5 and a reserve bobbin 6 are held. The supply bobbin 5 delivers a thread 3 which is transferred for drawing and texturing in the processing station 1. An end of a thread of the supply bobbin 5 is interconnected with a start of a thread of the reserve bobbin 6 by means of a thread knot. A continuous unwinding of the thread 3 is implemented after the end of the supply bobbin 5. The end of the thread of the reserve bobbin 6 is then connected to the start of the thread of a new supply bobbin 5.

The thread 3 is unwound from the supply bobbin 5 by a first delivery system 7.1. The delivery system 7.1 is driven via a drive 8.1. In this example embodiment, the delivery system 7.1 is formed by a driven delivery roller and a freely rotatable roller around which the thread is wound multiple times. In the continuing path of the thread, a heating device 9, a cooling device 10 and a texturing unit 11 are disposed downstream of the delivery system 7.1. The texturing unit 11 is driven via a texturing drive 11.1. The texturing unit 11 is preferably designed as a friction twister in order to create a false twist on the thread which produces a crimping of the individual filaments of the thread.

A second delivery system 7.2 which is driven by the drive 8.2 is disposed downstream of the texturing unit 11 in order to draw the thread. The delivery system 7.2 is identical in design to the first delivery system 7.1, wherein the second delivery system 7.2 is operated with a higher circumferential speed for drawing the thread. The synthetic thread 3 is thus textured and simultaneously drawn within the processing station 1. Following the crimping of the thread 3, said thread is guided by a third delivery system 7.3 to a bobbin station 2. The delivery system 7.3 is driven by the drive 8.3.

The bobbin station 2 has a bobbin holder 13 which carries a bobbin 14. The bobbin holder 13 is designed as pivotable and can be operated manually or automatically to exchange the bobbin 14. A drive roller 15 which is driven by a roller drive 15.1 is assigned to the bobbin holder 13. To position the thread at the periphery of the bobbin 15, a traversing unit 12 which has a drivable traversing thread guide is assigned to the bobbin station 2. To do this, the traversing thread guide is driven in an oscillating manner via the traversing drive 12.1.

The traversing drive 12.1 and the roller drive 15.1 of the bobbin station 2 are designed as individual drives and are connected to a machine control unit 16. The drives 8.1, 8.2 and 8.3 of the delivery systems 7.1, 7.2 and 7.3 and the texturing drive 11.1 of the texturing unit 11 of the processing station 1 are designed as individual drives and are coupled to the machine control unit 16.

A thread tension is measured continuously on the running thread 3 in a measuring station between the delivery system 7.2 and the delivery system 7.3 in order to monitor the texturing process. A thread tension measuring device 17 which has a thread tension sensor 17.1 and a measuring signal pick-up 17.2 is provided for this purpose. The thread tension measuring device 17 is connected to a data processing device 18 designed as a diagnostic unit. Reference is additionally made to FIG. 2 for further explanation of the diagnostic unit 18.

FIG. 2 shows schematically the diagnostic unit 18 for analyzing the thread tension measuring signals. In this example embodiment, the diagnostic unit 18 comprises a learning processor 20. The learning processor 20 is connected directly to the measuring signal pick-up 17.2 of the thread tension measuring device 17. The learning processor 20 is designed as programmable and preferably has a neural network to run a machine learning program. The machine learning program comprises at least one machine learning algorithm in order to be able to perform extensive analyses of the thread tension measuring signals with artificial intelligence.

An input unit 22 and an output unit 23 are assigned to the learning processor 20. The connection between the learning processor 20 and the thread tension measuring device 17, the input unit 22 and the output unit 23 can be established in each case by a wired or wireless connection. Particularly in the case of a wireless connection, it is possible that individual units do not have to be held directly on the texturing machine. Learning programs which are located in a virtual space can thus also be used. The possibility thus exists to dispose the learning processor 20 independently from the input unit 22 and the output unit 23.

The thread tension measuring signals transmitted by the measuring signal pick-up 17.1 are analyzed with the machine learning program in the learning processor 20. The machine learning program has at least one machine learning algorithm which performs a structured analysis of the sequence of thread tension measuring signals occurring in a time interval by means of a neural network for the early diagnosis of one of a plurality of fault sources. The measuring signal changes in the thread tension measuring signals occurring in the time sequence are analyzed in order to reveal typical features for the identification of a specific fault source.

In the example embodiment shown in FIG. 2, the input 22 is assigned to the learning processor 20. In this respect, the machine learning program can be trained continuously with fault graphs of known fault sources. This learning phase of the machine learning algorithm normally reaches maturity and therefore an operational status of completed training after an operating period. In this state, the diagnostic unit 18 is operated without an input unit 22. It is correspondingly also possible to use the diagnostic unit 18 in known texturing processes from the outset with a learning program with a trained machine algorithm. The use of an input unit then becomes superfluous.

If, in the case of a trained system, an error graph of an unknown fault source occurs which is not identifiable by the machine learning algorithm, the learning program of the learning processor can be exchanged or retrained at a central location. The error graph of the unknown fault source is first transmitted directly to the central training location so that existing machine learning algorithms can already be trained.

FIG. 3 shows an example embodiment of a time sequence of thread tension measuring signals in a diagram. The level of the thread tension T is plotted on the y-axis and the time t on the x-axis of the diagram. The characteristic of the measuring signals reveals an abrupt increase in the thread tension which occurs for only a short time interval from time $t_1$ to time $t_2$. The thread tension measuring signals before and after the increase are insignificant. The measuring signal sequence indicates a fault source in the form of a thread knot which has passed through the measuring station. In order to identify a fault source of this type, the typical measuring signal characteristic is supplied to the learning program in advance so that characteristic features of this type are identifiable in a later analysis of measuring signal sequences.

If a thread knot in the thread passes through the measuring station during the monitoring of the texturing process, a similar measuring signal sequence is generated by the measuring signal pick-up 17.1 and is fed to the diagnostic unit 18. Due to the analysis of the measuring signal sequence performed in the learning processor, the typical characteristic measuring signal changes are identified and the fault source concerned is identified. It is irrelevant here whether the thread tension change exceeds a threshold value or remains within a permissible tolerance range.

Since not only product defects occur as a fault source in a texturing process, a differentiated and, in particular, an extended analysis and diagnosis of a fault source are desired. For this purpose, a further example embodiment of the device according to the invention is shown in FIG. 4, as would be used, for example, in a texturing process according to FIG. 1. In this case, the diagnostic unit 18 comprises a thread tension evaluation unit 19 which is connected directly to the thread tension measuring device 17. The measuring signals of the measuring signal pick-up 17.2 are thus fed to the thread tension evaluation unit 19. Changes over time in the measuring signals are recorded in a sequence within the thread tension evaluation unit 19 and are generated as an analysis graph. The measuring signals are compared in parallel with a threshold value. The thread tension measuring signal is normally compared with an upper limit value and a lower limit value of the thread tension. As soon as an impermissible tolerance deviation in the thread tension is detected, the momentary measuring signal characteristic of the thread tension is recorded and generated as an error graph.

Depending on whether an analysis graph without a threshold value being exceeded or an error graph with a threshold value violation is present, said graph is transferred to a learning processor 20. The learning processor 20 is adapted accordingly in its machine learning algorithm in order to be able to perform corresponding analyses to diagnose the cause of the fault.

FIGS. 5 and 6 show an analysis graph without a threshold value violation and an error graph with a threshold value violation, respectively. The thread tension measuring signal is compared with an upper limit value and a lower limit. In the analysis graph and the error graph, the upper limit value is denoted by the reference letters UL and the lower limit value by the reference letters LL. The thread tension T is plotted on the y-axis and the time t on the x-axis for this purpose. In the case of the signal characteristic of the thread tension measuring signals shown in 5, no exceeding of the upper limit value and no understepping of the lower limit value are evident. In this respect, the thread tension signal change caused by a fault source is within the permissible range. A thread knot, for example, could nevertheless represent an impermissible defect in a fabric in the downstream process.

In the error graph shown in FIG. 6, the thread tension measuring signals exceed the upper limit UL so that a threshold value violation and therefore an impermissible deterioration in the quality of the thread are present. The method according to the invention and the device according to the invention are thus independent from whether the process disruption caused by a fault source causes a permissible or impermissible thread tension change on the thread.

As is evident from the diagram in FIG. 4, a plurality of fault graphs are predefined for the learning processor via the input unit. A fault graph contains the thread tension measuring signal characteristic which is typical of the specific fault source. The machine learning program can thus be trained and extended in order to enable a unique diagnosis and identification of the fault sources.

Figure 7:
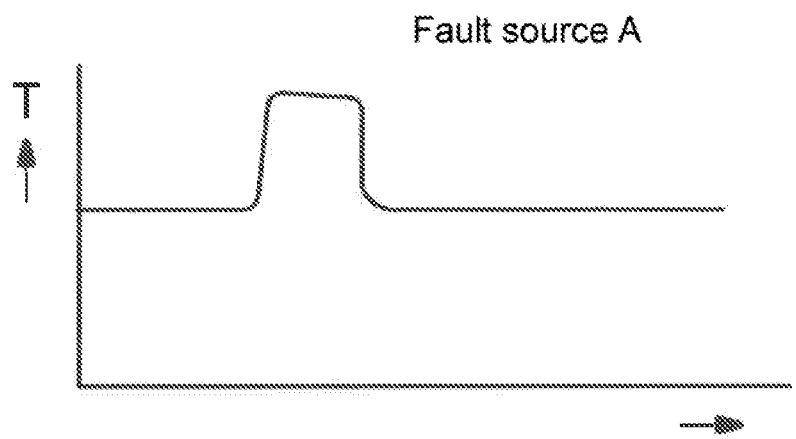

In FIGS. 7 to 11, a plurality of fault graphs of different fault sources are characterized schematically, by way of example, by a typical thread tension measuring signal sequence. Each of the fault graphs represents a typical fault source such as those which can occur in the texturing process. The fault graph according to FIG. 7 shows a signal characteristic of the thread tension in the case of a thread knot which is denoted here as the fault source A.

Figure 8:
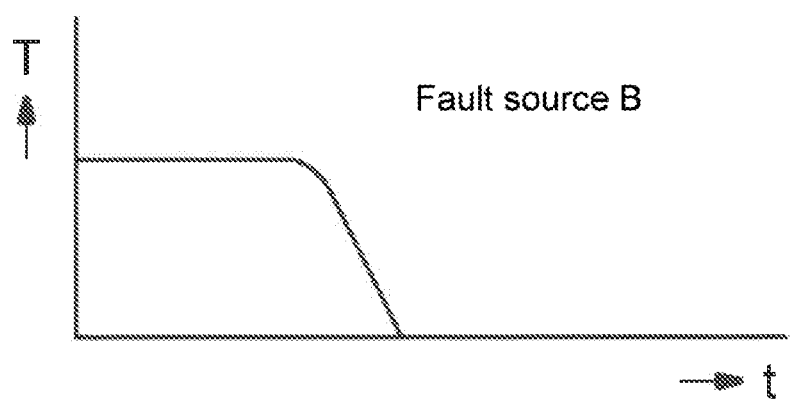

The fault source B shown in FIG. 8 shows a sudden drop in the thread tension, as could be caused, for example, by a thread break or an operating error. Here, the thread tension on the thread tension sensor suddenly collapses completely.

Figure 9:
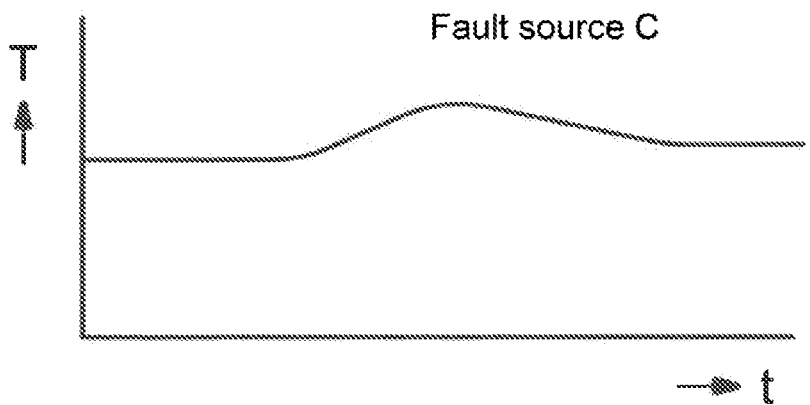

The fault graph shown in FIG. 9 defines the fault source C. The fault source C could, for example, represent a condition of wear on one of the process units or on a thread-guiding element.

Figure 10:
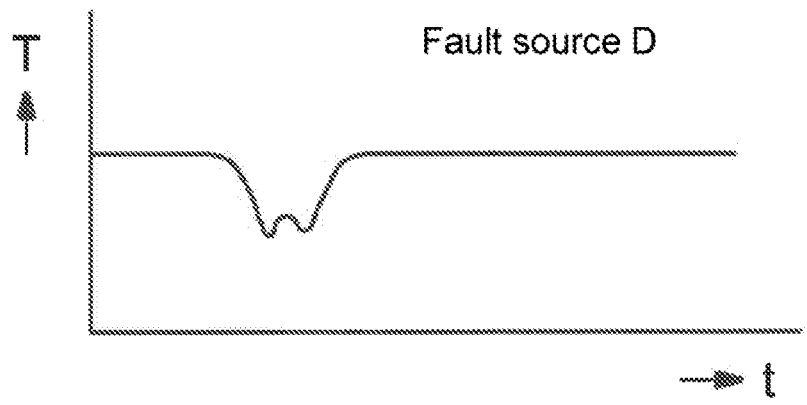

In the fault graph shown in FIG. 10, a momentary thread tension loss occurs which is assigned here to the fault source D. A process fault could be present here during the bobbin change in the bobbin station.

Figure 11:
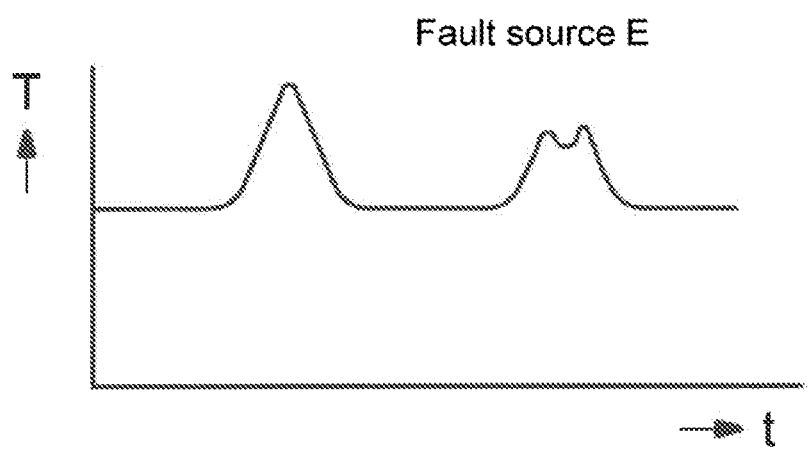

A recurring excessive increase in the thread tension measuring signal is evident in the fault graph shown in FIG. 11. The associated fault graph is assigned in this case to the fault source E. The fault source E could lie, for example, in an uneven texturing of the thread.

In this respect, a specific process fault or a specific operating error or a specific product defect is assigned to each of the fault sources A to E. The fault graphs shown in FIGS. 7 to 11 and their fault sources are presented by way of example. In a texturing process as shown in FIG. 1, a multiplicity of fault sources can occur which are based on a unique measuring signal sequence for diagnostic identification.

In the example embodiment of the device according to the invention shown in FIG. 4, the diagnostic unit 18 is connected via the learning processor 20 directly to a machine control unit 16. As shown in FIG. 1, the machine control unit 16 is coupled to the drives and actuators of the process units of the processing station 1 which are controlled and regulated to perform the texturing process. In this respect, a process intervention is possible immediately following identification and diagnosis of a fault source. Thus, for example, in the event of a diagnosis of the fault source A which is caused by a thread knot, a bobbin change could be initiated in the bobbin station 2 so that the thread knot is wound at the end or at the start of a bobbin. Corresponding maintenance work can similarly be instigated through early diagnoses of signs of wear. Preventive repairs and maintenance can thus be carried out on the process units in order to maintain the quality in the production of the crimped thread as constant as possible. The example embodiment of the device according to the invention shown in FIG. 4 is still in a learning phase. As soon as the training of the machine learning algorithm for identifying all known fault sources is completed, the diagnostic unit 18 can be operated without an input unit 22. The thread tension signals are then fed immediately to the learning processor 20 and are directly analyzed.

The invention claimed is:

1. A method for monitoring a texturing process for producing crimped threads, in which a thread tension is measured continuously on a textured thread and in which thread tension measuring signals are captured and analyzed continuously, at least in one time interval, wherein a sequence of the thread tension measuring signals occurring in the time interval is analyzed with a machine learning program for diagnosis of one of a plurality of fault sources.

2. The method as claimed in claim 1, wherein the sequence of the thread tension measuring signals is captured and analyzed as an analysis graph.

3. The method as claimed in claim 1, wherein, by a diagnostic device, the sequence of thread tension measuring signals is captured and analyzed as an error graph if a thread tension threshold value is exceeded.

4. The method as claimed in claim 1, wherein the analysis of the thread tension measuring signals is performed by at least one machine learning algorithm of the machine learning program.

5. The method as claimed in claim 4, wherein one of the fault sources is identified by the machine learning algorithm from analyzed sequences of measuring signals or from analyzed analysis graphs or from analyzed error graphs.

6. The method as claimed in claim 5, wherein a plurality of fault graphs are assigned to the analysis graphs and/or the error graphs, wherein each of the fault sources is defined by one of the fault graphs.

7. The method as claimed in claim 6, wherein the machine learning algorithm has attained an operational status of completed training after a learning phase.

8. The method as claimed in claim 7, wherein an operating error, an incorrect setting of a process unit, a material defect, wear of a thread-guiding element and/or a thread knot is/are one of the fault sources.

9. The method as claimed in claim 8, wherein a control command for a process change is triggered following identification of the fault source or following assignment to one of a plurality of fault graphs.

10. A device for monitoring a texturing process for producing crimped threads with a thread tension measuring device for measuring a thread tension at a measuring station and with a data analysis device for analyzing thread tension (T) measuring signals of the thread tension measuring device, wherein the data analysis device is formed by a diagnostic unit by means of which the thread tension (T) measuring signals are analyzable with a machine learning program for identifying a fault source.

11. The device as claimed in claim 10, wherein the diagnostic unit has a programmable learning processor to run the machine learning program.

12. The device as claimed in claim 11, wherein the learning processor is optionally coupled for training purposes to an input unit by means of which one or more determined thread tension fault graphs are loadable.

13. The device as claimed in claim 11, the learning processor is coupled to an output unit by means of which an identification of the fault source and/or an assignment to one of a plurality of fault graphs is visualizable.

14. The device as claimed in claim 11, wherein the learning processor has a neural network to run the machine learning program.

15. The device as claimed in claim 11, wherein the learning processor is physically separated from an input unit and an output unit.

16. The device as claimed in claim 10, wherein the diagnostic unit is connected to a machine control unit by means of which a control command for a process change is executable.

* * * * *